US007824417B2

(12) United States Patent
Magnusson et al.

(10) Patent No.: US 7,824,417 B2
(45) Date of Patent: Nov. 2, 2010

(54) GUIDE FOR A MEDICAL DEVICE

(75) Inventors: Anders Magnusson, Uppsala (SE); Per Egnelöv, Uppsala (SE)

(73) Assignee: Aprio Medical AB, Uppsala (SE)

( * ) Notice: Subject to any disclaimer, the term of this patent is extended or adjusted under 35 U.S.C. 154(b) by 1392 days.

(21) Appl. No.: 10/494,255

(22) PCT Filed: Sep. 1, 2003

(86) PCT No.: PCT/SE03/01349

§ 371 (c)(1),
(2), (4) Date: May 4, 2004

(87) PCT Pub. No.: WO2004/021898

PCT Pub. Date: Mar. 18, 2004

(65) Prior Publication Data

US 2004/0260312 A1 Dec. 23, 2004

Related U.S. Application Data

(60) Provisional application No. 60/407,959, filed on Sep. 5, 2002.

(30) Foreign Application Priority Data

Sep. 5, 2002 (SE) .................................... 0202633

(51) Int. Cl.
*A61B 19/00* (2006.01)
(52) U.S. Cl. .................................... 606/130; 74/490.01
(58) Field of Classification Search ................ 606/129, 606/130; 600/417, 429; 700/245; 604/164.12, 604/165.01, 170.02; 382/132; 74/490.01
See application file for complete search history.

(56) References Cited

U.S. PATENT DOCUMENTS 2,697,433 A * 12/1954 Zehnder ..................... 606/96
3,021,842 A   2/1962 Flood
3,308,675 A * 3/1967 Jonsson .................... 74/471 R (Continued)

FOREIGN PATENT DOCUMENTS

DE    198 08 220 A1    9/1999

(Continued)

*Primary Examiner*—Michael J Milano
*Assistant Examiner*—Victor X Nguyen
(74) *Attorney, Agent, or Firm*—Foley & Lardner LLP

(57) ABSTRACT

The invention provides a puncturing guide (1, 16) for guiding a puncturing needle into a target site within the body of a patient. The puncturing guide (1, 16) comprises a base plate (2, 17), a needle guide (3, 18), a retainer (4, 19) for securing the needle guide (3, 18) to the base plate (2, 17), a first segment (7, 20) of a first semi-sphere, a second segment (8, 21) of a second semi-sphere, and a needle guide (3, 18) attached to the second segment (8, 21). During a positioning operation, the second segment (8, 21) slides on the first segment (7, 20), so that the needle guide (3, 18) is movable around the center of the first semi-sphere, which is in level with the underside of the base plate (2, 17), thereby providing the possibility to position the tip of a puncturing needle at a puncturing point on the patient's skin and then, in a separate operation, set the entrance angle of the puncturing needle without changing its entrance point.

19 Claims, 5 Drawing Sheets

U.S. PATENT DOCUMENTS

| | | | |
|---|---|---|---|
| 4,608,977 A | | 9/1986 | Brown |
| 4,733,661 A | | 3/1988 | Palestrant |
| 4,805,615 A | | 2/1989 | Carol |
| 5,094,243 A | * | 3/1992 | Puy et al. ................ 600/459 |
| 5,201,742 A | * | 4/1993 | Hasson .................... 606/130 |
| 5,263,956 A | | 11/1993 | Nobles |
| 5,767,839 A | * | 6/1998 | Rosenberg ................ 345/161 |
| 5,871,487 A | * | 2/1999 | Warner et al. ............ 606/130 |
| 6,289,263 B1 | * | 9/2001 | Mukherjee ................ 700/245 |
| 6,966,876 B2 | * | 11/2005 | Irion et al. ................ 600/102 |
| 2002/0049451 A1 | | 4/2002 | Parmer et al. |

FOREIGN PATENT DOCUMENTS

| | | |
|---|---|---|
| JP | 10-248849 A | 9/1998 |
| JP | 2001-128974 A | 5/2001 |

* cited by examiner

GUIDE FOR A MEDICAL DEVICE

FIELD OF THE INVENTION

The present invention relates generally to a guide for guiding a medical instrument to a target site within a patient's body, and more particularly to a puncturing guide for guiding a puncturing instrument, e.g. a biopsy instrument, to a target site, the position of which has been determined by means of computerized tomography (CT), magnetic resonance imaging (MRI), ultra sound or the like.

BACKGROUND OF THE INVENTION

CT is used to provide doctors with a cross-sectional picture of a patient's internal organs and tissues; and if a puncturing operation is to be performed, the CT-scanner provides the doctor with image data from which the doctor determines the puncturing position, the direction and the depth for a puncturing device so as to reach the target site. In some cases, the puncturing device is manipulated without employing any device for guiding the puncturing needle, but often some kind of guiding device is used.

A variety of guides employed to properly position a medical instrument within the body of a patient are known in the state of the art. U.S. Pat. No. 4,733,661 discloses a handheld guidance device for use in conjunction with a CT scanner. This guidance device comprises a base including a bubble level and a needle support arm pivotally secured to the base, and a cooperating protractor indicates the relative angular relationship between the needle support arm and the base. Needle guides are provided on the support arm for slidingly supporting a catheter at a desired angle as the catheter is inserted into the body of the patient. With this device, the direction to the target site has to be set with two separate operations, one that adjusts the elevation angle of the support arm and one that rotates the guidance device.

In U.S. Pat. No. 5,263,956 is shown a ball joint for holding a neurosurgery tool in a predetermined orientation relative to a patient's skull. The ball joint, which is provided with a bore, is rotatably positioned in a socket formed in a plate, and a neurosurgery tool can be positioned in the bore to extend through the bore into the patient's brain. Set screws are provided to hold the neurosurgery tool stationary relative the bore of the ball and to hold the ball stationary relative the plate. A retainer ring holds the ball against the plate. The bottom of the plate is provided with spikes for gripping the skull.

In DE-19,808,220 A1 is shown another guiding device. This guiding device comprises an attachment plate and a ball joint for guiding a needle. The bottom side of the attachment plate is provided with an adhesive, so that the guiding device can be securely positioned on a patient's skin. The ball joint is provided with a clamping means, which allows the needle to be positioned in a continuously variable spatial direction.

U.S. Pat. No. 3,021,842 discloses a similar guiding device that also comprises a ball joint, which in this case is provided with a pinion. With the pinion, the ball can be turned in a socket through a wide range of angles.

A common feature of the devices known in the state of the art is that the point of entrance for a puncturing device, e.g. puncturing needle or a biopsy needle, through a patient's skin varies with the entrance angle, or, with other words, the rotation centre of the directional adjusting means is not located at the entrance point. This means that it is not possible to position the distal tip of a puncturing device at the puncturing point in a first operation and then, in a second operation, set the entrance angle of the puncturing device without changing the entrance point of the puncturing device. In some applications this is a considerable disadvantage, as will be described below.

The object of the present invention is to refute the above-identified drawback with known devices in the art of puncturing guidance.

SUMMARY OF THE INVENTION

The above-mentioned object is achieved by the present invention as disclosed in the present specification.

Preferred embodiments are set forth in the following description.

Thus, the object is achieved by arranging a puncturing guide having provided with a needle guide that is movable around a point that coincides with the defined puncturing entrance point of a puncturing device, e.g. a biopsy needle. With such a puncturing guide, the tip of the puncturing device may be positioned at the puncturing point in a first operation and, in a subsequent operation, the entrance angle can be set without moving the position of the needle tip.

In one embodiment, the puncturing guide according to the present invention comprises a base plate having a flat bottom and being provided with three flat legs for attachment on a patient's skin, a tubular needle guide, in which a puncturing needle is to be inserted, and a retainer, which secures the needle guide to the base plate by means of a bayonet coupling. In the center of the base plate, a first semi-sphere is provided, and a bore extends from the top of the semi-sphere to the bottom of the base plate. The outer radius of this first semi-sphere is the same as the inner radius of a segment of a second semi-sphere being provided on the shaft of the needle guide. During an angle adjusting operation, the segment of the second semi-sphere slides on the first semi-sphere, with the tubular needle guide pointing at an object beneath the base plate through the bore in the first semi-sphere. For this puncturing guide, the centre of the first semi-sphere constitutes the rotational centre of the needle guide, and it is therefore possible to position the tip of a puncturing needle at a puncturing point located at a patient's skin and then set the entrance angle of the puncturing needle without changing its entrance point.

DESCRIPTION OF THE INVENTION

Figure 1:
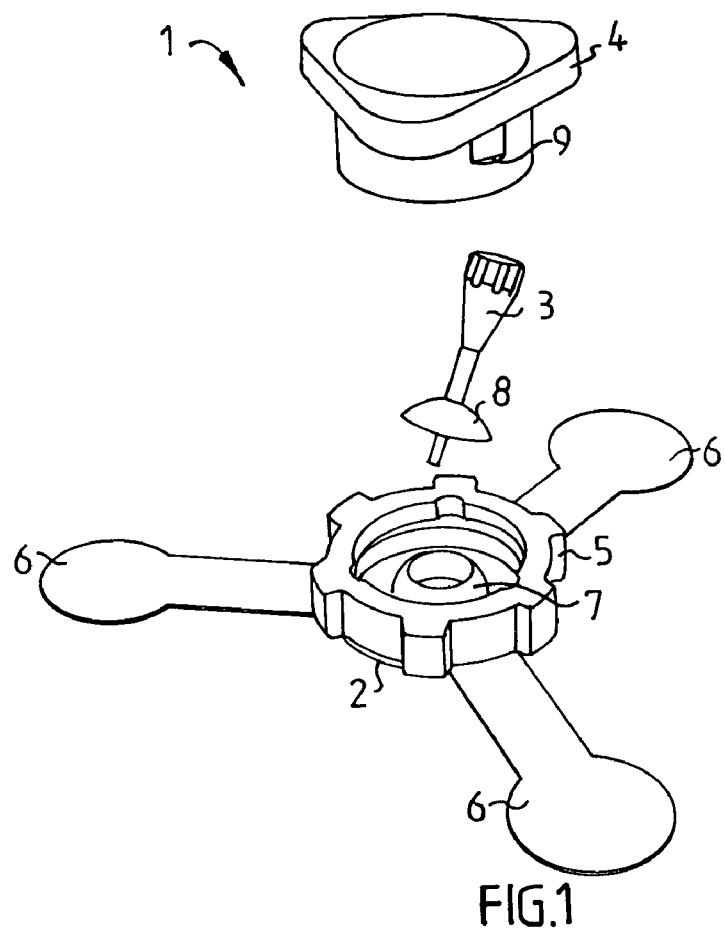
FIG. 1 illustrates a first embodiment of a puncturing guide according to the present invention in a disassembled state.

A first embodiment of a puncturing guide according to the present invention will be described in conjunction with FIG. 1 to FIG. 3. In FIG. 1 is shown a puncturing guide 1 in a disassembled state. The puncturing guide 1 comprises basically a base plate 2, a tubular needle guide 3 and a retainer 4. The base plate 2, in turn, comprises a central, ring-shaped member 5 and flat legs 6, e.g. three, the undersides of which preferably are provided with a suitable adhesive for attachment to a patient's skin. On the central part of the ring-shaped member 5, a first sliding surface in the form of a first segment 7 of a first semi-sphere is provided. In the center of this first semi-sphere, a bore is formed, which extends from the top of the semi-sphere to bottom of the base plate 2. The outer radius of this first semi-sphere is the same as the inner radius of a second sliding surface in the form of a second segment 8 of second semi-sphere, which is provided on the shaft of the needle guide 3. In this preferred embodiment, the distance between the distal end of the needle guide 3 and the second segment 8 is equal to the outer radius of the first semi-sphere. The lower part of the retainer 4 is ring-shaped, while its upper part has been enlarged to a triangular shape, thereby providing a better grip for a user. The lower inside of the retainer 4 is chamfered (as is best seen in FIG. 3), with the chamfering corresponding to the outer curvature of the second segment 8 of the second semi-sphere. The upper inside of the hollow retainer 4 is also chamfered and narrows downwards to a diameter that is less than the diameter of the second segment 8. The retainer 4 is thereby provided with an internal waist. The outside of the lower ring-shaped part of the retainer 4 is provided with projections 9, which fit into grooves in the inside of the ring-shaped member 5, thereby providing a bayonet coupling between the base plate 2 and the retainer 4.

Figure 2:
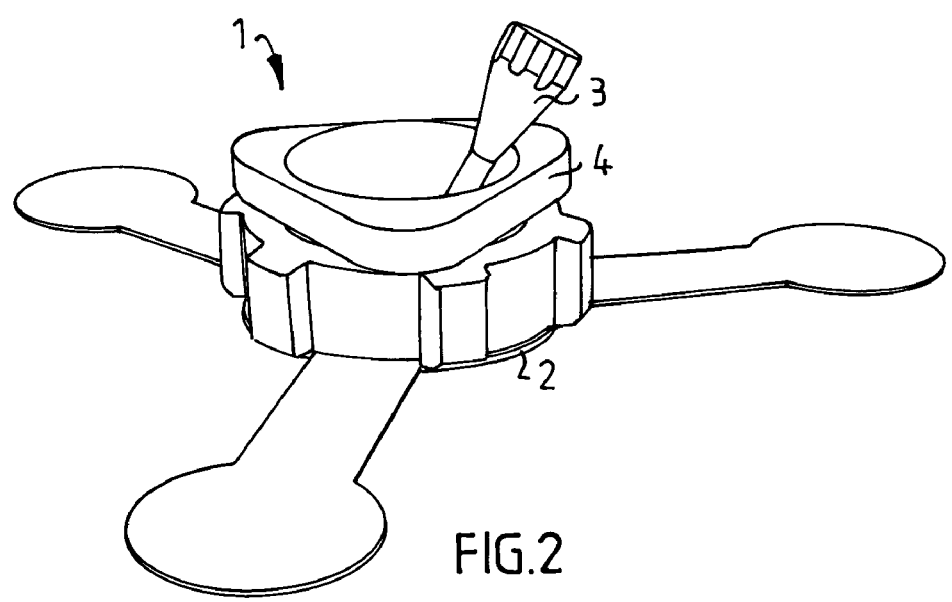
FIG. 2 illustrates the puncturing guide of FIG. 1 in an assembled state.
Figure 3:
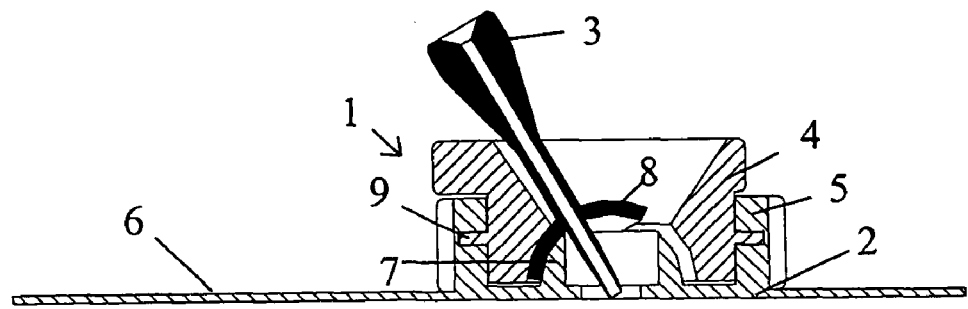
FIG. 3 shows the cross-section of the puncturing guide according to FIG. 2.

FIG. 2 illustrates the puncturing guide 1 in an assembled state. Here, the needle guide 3 is secured to the base plate 2 by the retainer 4, whose chamfered lower inside presses the inside of the second segment 8 (not visible in the figure) into contact with the first segment 7 (not visible in the figure). In this state, the distal end of the needle guide 3 is in level with the flat underside of the base plate 2. As mentioned before, the center of the first semi-sphere constitutes the rotational center of the needle guide 3, and since the center of the first semi-sphere is located at the bottom of the base plate 2, the needle guide 3 rotates around a point located at the surface of an object, such as the skin of a patient, to which the base plate 2 of the puncturing guide 1 has been attached. This means that a puncturing needle (e.g. biopsy needle) inserted into the needle guide 3 can be positioned in different directions without changing the entrance point through a patent's skin for the distal tip of this needle. As will be described in more detail below, during the directional positioning of the needle guide 3, the retainer 4 does not fixedly lock the needle guide 3 to the base plate 2, i.e. the bayonet coupling is not fully tightened, so the second segment 8 can slide on the first segment 7.

The cross-section of the puncturing guide 1 is shown in FIG. 3. As can be seen in the figure, the projections 9 on the outside of the ring-shaped part of the retainer 4 are in engagement with corresponding grooves in the inside of the ring-shaped member 5, thereby providing a bayonet coupling between the retainer 4 and the base plate 2. It should also be noted that the chamfered lower inside of the retainer 4 is in contact with the upper side of the second segment 8 and that the underside of the second segment 8 is in contact with the first segment 7. When the bayonet coupling is not fully tightened, the second segment 8 can slide on the first segment 7, and the needle guide can be positioned in any angular direction within a certain angular interval, as will be explained below. When the bayonet coupling is tightened, the needle guide 3 is locked in a fixed position by the friction between the first segment 7 and the second segment 8 and by the friction between the second segment 8 and the chamfered inside of the retainer 4. Further, the special advantage of the puncturing guide 1 should also be recognized from FIG. 3. Due to the fact that the second segment 8 slides on the first segment 7, the needle guide 3 rotates around the center point of the first semi-sphere, which in use is located at a patient's skin, so that the entrance point for the distal tip of a needle inserted in the needle guide 3 remains essentially the same irrespective of the angular orientation of the needle guide 3.

Before describing an example of how the puncturing guide according to the present invention may be used in conjunction with a laser, or any suitable alignment equipment, to guide a puncturing needle into a target site within a patient's body, a few remarks can be made regarding the puncturing guide 1 described with reference to FIG. 1 to FIG. 3. As should be clear from FIG. 3, the chamfering of the lower inside of the retainer 4 corresponds preferably to the outer radius of the second segment 8, thereby providing a secure locking for the needle guide 3 between the base plate 2 and the retainer 4. Further, as mentioned above, the needle guide 3 can assume any angular orientation within a certain angular interval. In particular from FIG. 3 it should be clear that this angular interval is determined by the diameter of the bore through the first semi-sphere provided in the center of the ring-shaped member 5 as well as by the size of the second segment 8 provided on the shaft of the needle guide 3. In this first embodiment of a puncturing guide, the needle guide 3 is locked by means of a bayonet coupling between the base plate 2 and the retainer 4. It should, however, be clear that other types of attachment and retainer means could be used. For example, the ring-shaped member and the retainer could be threaded into each other, or some kind of compressible or expandable clamping means could be used, or a screw could be provided that secures the retainer to the base plate and locks the needle guide in a fixed orientation.

According to a preferred embodiment of the present invention the part of the needle guide (3, 18) facing the defined puncturing entrance point is reinforced with reinforcement means having an essentially tubular shape. The reinforcement means is not shown in the figures. It is preferably an integral part of the needle guide. The reinforcement means serves two purposes. One is to strengthen the needle guide and the other is to make the needle guide visible on images obtained by e.g. X-ray or magnetic resonance techniques. If MRI is used the reinforcement means should preferably be made from a non-magnetic metal, e.g. non-magnetic stainless steel.

Figure 4:
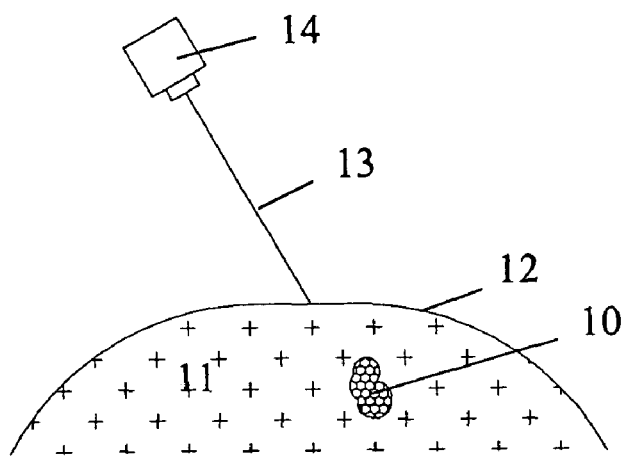
FIG. 4 illustrates schematically a target site embodied in tissue within the body of a patient.

In order to fully appreciate the special advantage of having a puncturing guide provided with a needle guide being movable around a point that coincides with the entrance point of a puncturing needle to be introduced into the body of a patient, an illustrative, non-limiting example of how such a puncturing guide may be used in conjunction with a laser will be described below. It should, however, be understood that a puncturing guide according to the present invention can be used in any medical guiding procedure known in the state of the art. FIG. 4 illustrates schematically a target site 10, such as an internal organ, embodied in surrounding tissue 11 under the skin 12 of a patient. The position of the target site 10 may have been determined by a CT scanner, which provides a doctor with image data from which the depth of the target site, the suitable puncturing point through the skin 12 as well as the suitable entrance angle for a puncturing needle can be determined. In this specific example, a laser beam 13 from a laser 14 indicates the entrance angle and the puncturing point at the skin 12.

Figure 5:
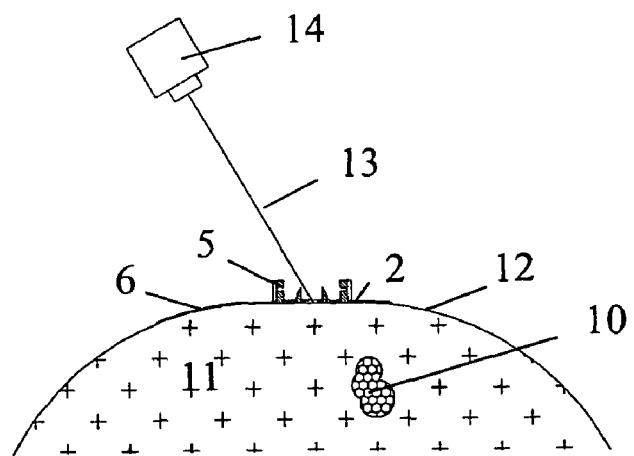
FIG. 5 illustrates schematically the first step in an alignment operation in which a puncturing guide according to the present invention is employed.

FIG. 5 illustrates schematically the first step of an alignment operation in which the puncturing guide 1 is employed. In this first step, the center of the bore through the first semi-sphere on the base plate 2 is positioned so that the laser spot on the skin 12, which indicates the puncturing point, is in the center of the bore. The base plate 2 is secured in this position by means of the adhesive provided at the undersides of the flat legs 6. As an alternative, the base plate 2 could be attached to the patient's skin 12 by means of adhesive tape.

Figure 6:
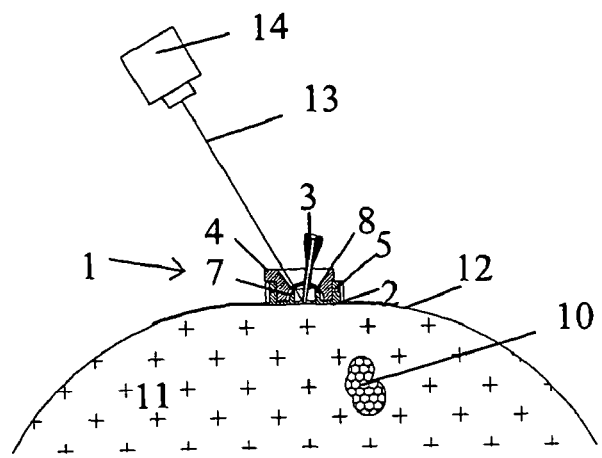
FIG. 6 illustrates schematically the second step in the alignment operation.

The second step of the alignment operation is schematically illustrated in FIG. 6. In the second step, the needle guide 3 is placed on the base plate 2, with the second segment 8 resting on the first segment 7, and the ring-shaped part of the retainer 4 is positioned in the ring-shaped member 5. The bayonet coupling between the base plate 2 and the retainer 4 is not yet tightened, so the second segment 8 can slide on the first segment 7. The needle guide 3 is not aligned with the laser beam 13, but it should be noted that the distal end of the needle guide 3 is positioned at the puncturing point indicated by the laser spot on the skin 12 of the patient.

Figure 7:
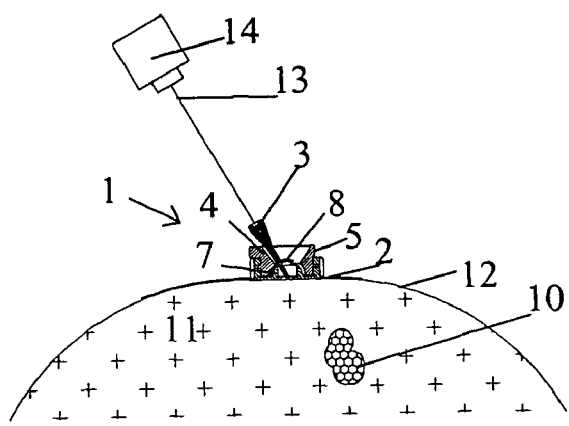
FIG. 7 illustrates schematically the third step in the alignment operation.

FIG. 7 illustrates schematically the completion of the third step of the alignment operation, in which the second segment 8 of the needle guide 3 is slid on the first segment 7 such that the proximal end of the needle guide 3 is positioned in the laser beam 13, i.e. a laser spot is visible in the center of the proximal end of the needle guide 3. When the needle guide 3 has been correctly positioned, the retainer 4 is tightened, which secures the needle guide 3 in position. Here the special advantage of the puncturing guide 1 is seen. Since the needle guide 3 may be moved around the center of the first semi-sphere, which is located at skin 12, the entrance position does not change during this angular positioning of the needle guide 3. Consequently, when the third step has been completed, the needle guide 3 is aligned with the laser beam 13, with the needle guide 3 pointing at the puncturing point indicated by the laser spot on the skin 12.

Figure 8:
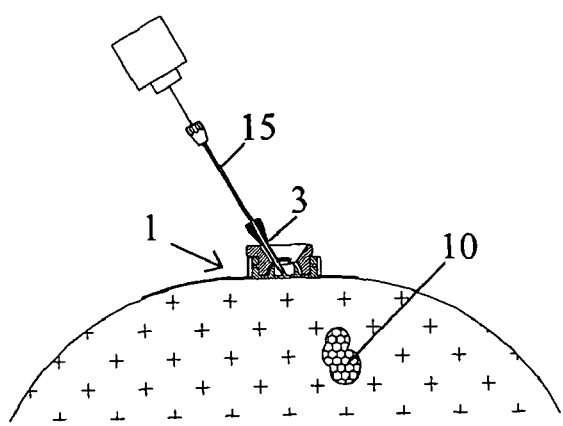
FIG. 8 illustrates schematically the first step in a puncturing operation following the alignment operation.
Figure 9:
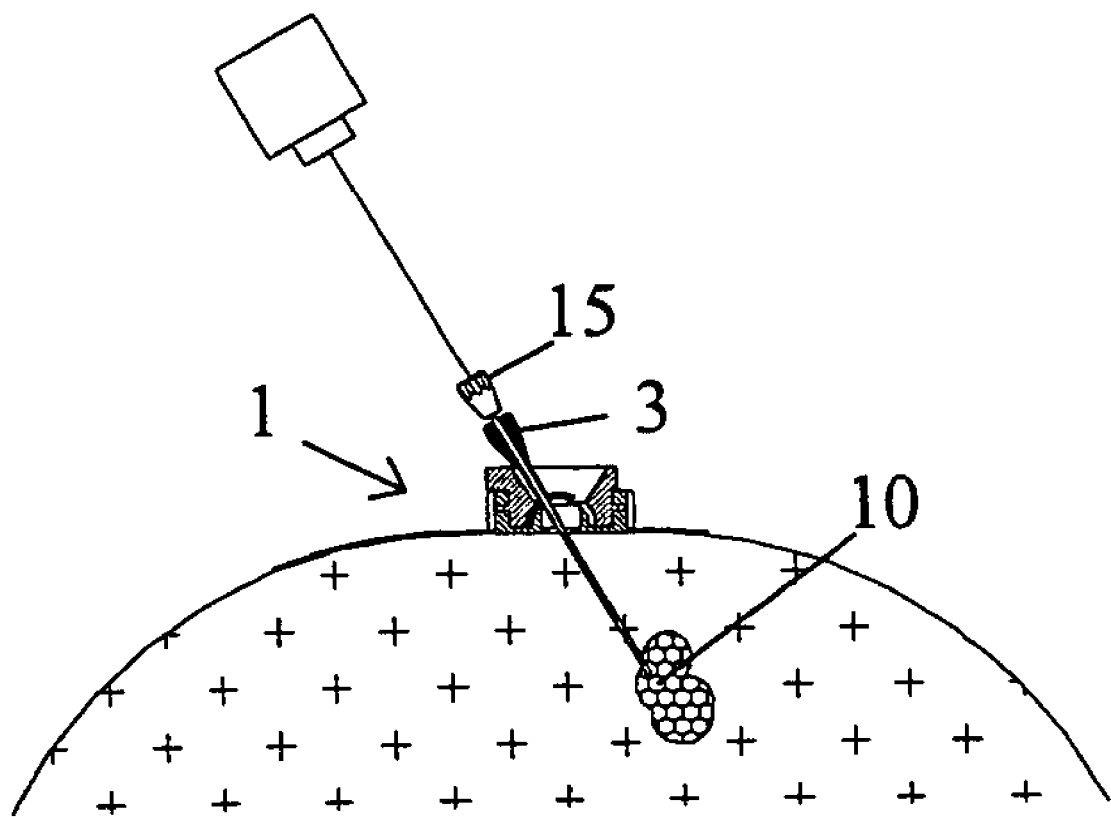
FIG. 9 illustrates schematically the second step in the puncturing operation.

The three steps described above have not involved any invasive operations and could actually be performed without any special medical training. For the sake of completeness, two more operations are shown in FIG. 8 and FIG. 9. In FIG. 8 is illustrated how a puncturing needle 15 is positioned inside the hollow needle guide 3, while FIG. 9 illustrates how the distal tip of the puncturing needle 15 is inserted into the target site 10, where a biopsy sample may be collected in a well known manner.

Figure 10:
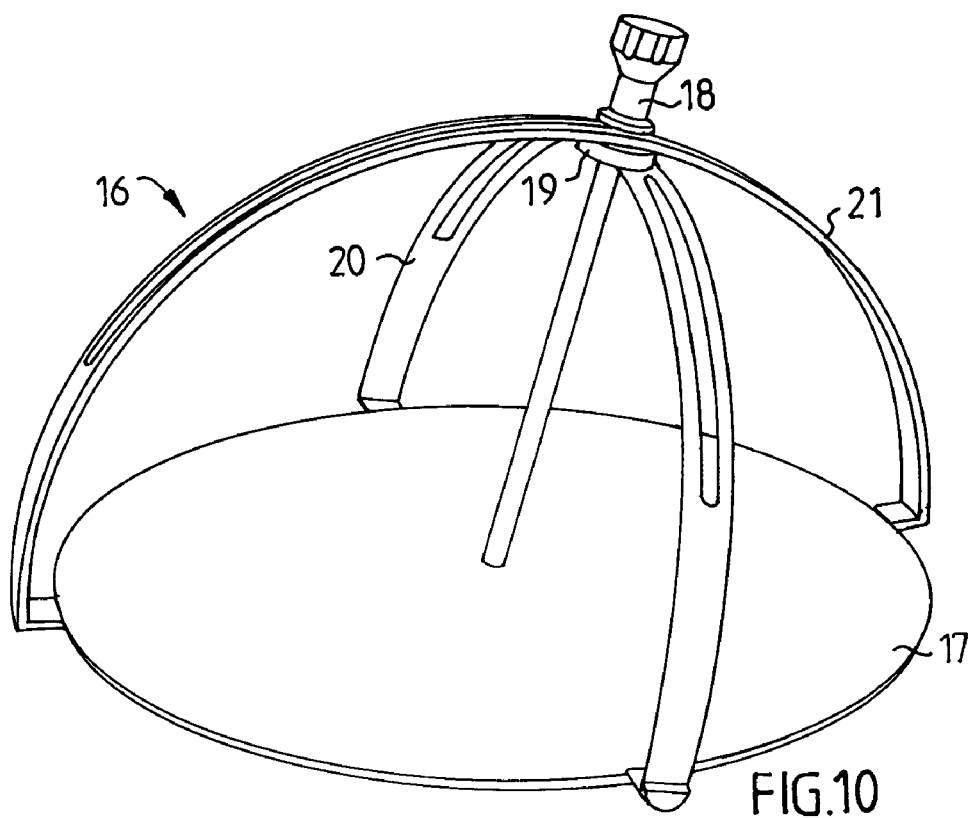
FIG. 10 illustrates a second embodiment of a puncturing guide according to the present invention in a first orientation.
Figure 11:
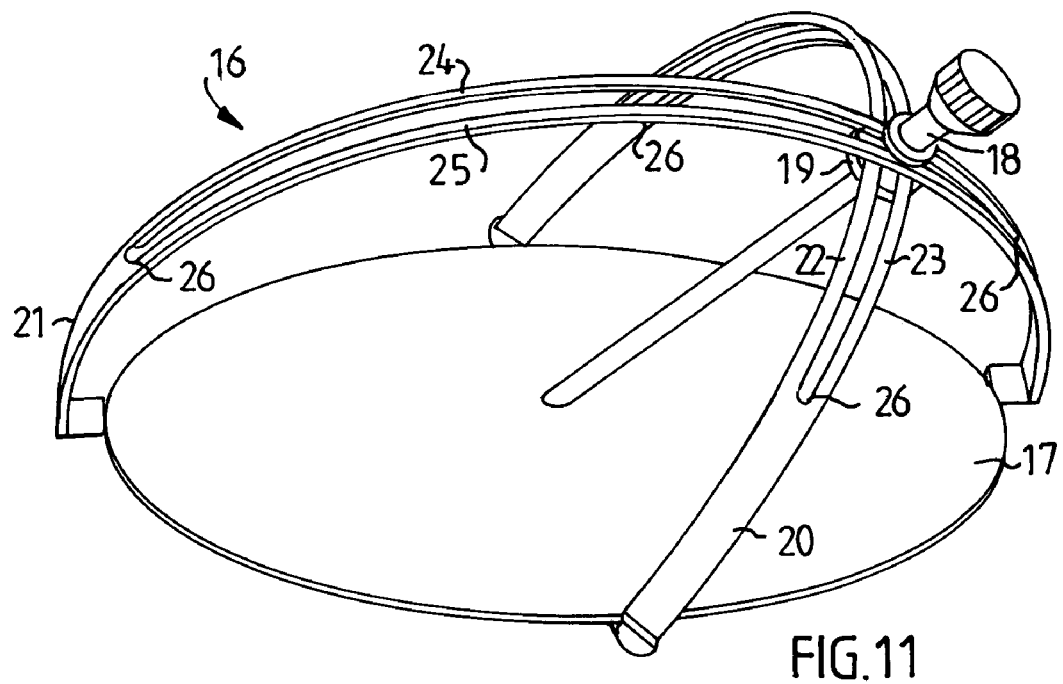
FIG. 11 illustrates the puncturing guide of FIG. 10 in a second orientation.

The possibility to divide the angular adjustment of the puncturing needle and its positioning at the puncturing point into two separate, independent steps is clearly dependent on the special feature of the present puncturing guide, i.e. that the needle guide is movable around the center point of the first semi-sphere, which center point in use is located at the puncturing point. This feature can be achieved with other arrangements. FIG. 10 and FIG. 11 illustrate a second embodiment of a puncturing guide 16 in a first and second orientation, respectively. The puncturing guide 16 comprises basically a flat base plate 17, a tubular needle guide 18, a ring-shaped retainer 19, a first segment 20 of a first semi-sphere, and a second segment 21 of a second semi-sphere.

The segments have the shapes of two semi-circular equally sized bows pivotally attached to the base plate 17 at positions separated by 90°, and that a slit is provided in each bow, wherein the needle guide 18 is adapted to be arranged in the slits at the intersection point of the bows wherein the needle guide 3, 18 is movable around a point that coincides with the defined puncturing entrance point. The distal end of the needle guide 18 is inserted in a bore in the center of the base plate 17. The inside of the ring-shaped retainer 19 is threaded and fits on a corresponding thread on the upper part of the needle guide 18. Before the retainer 19 is tightened, the needle guide 18 can slide inside the slits in the first and second segments 20, 21, with the distal tip of the needle guide being in contact, or almost in contact, with an object, such as the skin of a patient, beneath the base plate 17. As for the first embodiment described above, the center of the first semi-sphere constitutes the rotational center of the needle guide 18, which means that a puncturing needle inserted into the needle guide 18 can be positioned in different angular orientations without changing the entrance point through a patient's skin for the distal tip of this puncturing needle.

In FIG. 11, the reference numerals 22, 23 refer to two bow-shaped members between which the slit in the first segment 20 is provided (and the reference numerals 24, 25 refer to corresponding members of the second segment 21). The members 22, 23 (and the members 24, 25) can be detachable attached to each other by means of, for example, screws 26, so that the first and second segments 20, 21 can be removed from the puncturing guide 16. For some applications this feature may be advantageous if a doctor, in a final stage of the insertion procedure, wants to manipulate a puncturing needle without any assistance from a puncturing guide.

Although the present invention has been described with reference to specific embodiments, also shown in the appended drawings, it will be apparent for those skilled in the art that many variations and modifications can be done within the scope of the invention as described in the specification and defined with reference to the following claims.

The invention claimed is:

1. A puncturing guide for guiding a puncturing needle into a target site within a patient's body, comprising:
   a base plate adapted to be positioned on the patient's body at a defined puncturing entrance point,
   a needle guide adapted to guide the puncturing needle during insertion, and
   a retainer for securing the needle guide in a fixed position relative to the base plate,
   wherein the base plate is connected to a first section pivotable about a first axis and a second section pivotable about a second axis and attached to the needle guide such that the first and second sections are in a slidable arrangement,
   wherein said first and second sections cooperate in such a way that the needle guide is movable around a point that coincides with the defined puncturing entrance point,
   wherein the first section and the second section have shapes of two semi-circular equally sized bows pivotally attached to the base plate at positions separated by 90°,
   wherein a slit is provided in each bow,
   wherein the needle guide is adapted to be arranged in the slits at an intersection point of the bows such that the needle guide is movable around the point that coincides with the defined puncturing entrance point,
   wherein the retainer has internal threads that mate with corresponding external threads on an upper part of the needle guide such that the needle guide is rotated to tighten and loosen the retainer to secure the needle guide in the fixed position.

2. The puncturing guide according to claim 1, wherein a part of the needle guide facing the defined puncturing entrance point is reinforced with a reinforcement having an essentially tubular shape.

3. The puncturing guide according to claim 2, wherein the reinforcement is an integral part of the needle guide.

4. The puncturing guide according to claim 2, wherein the reinforcement is made from a material that makes the reinforcement visible on X-ray images.

5. The puncturing guide according to claim 4, wherein the reinforcement is made from a material compatible to magnetic resonance imaging.

6. The puncturing guide according to claim 1, wherein the internal threads of the retainer fit on the corresponding external threads of the needle guide such that the needle guide can be fixedly secured in a position by tightening the retainer with the needle guide, with the first and second sections being positioned therebetween.

7. A puncturing guide for guiding a puncturing needle into a target site within a patient's body, comprising:
  a base plate adapted to be positioned on the patient's body at a defined puncturing entrance point,
  a needle guide adapted to guide the puncturing needle during insertion, and
  a retainer for securing the needle guide in a fixed position relative to the base plate,
  wherein the base plate is connected to a first section and a second section attached to the needle guide such that the first and second sections are in a slidable arrangement relative to each other,
  wherein the first and second sections are configured to allow the needle guide to be set such that a tip of the puncturing needle is located at the defined puncturing entrance point,
  wherein the first and second sections are configured to permit adjustment of the needle guide, prior to insertion, such that an entrance angle of the puncturing needle can be adjusted while prohibiting movement of the needle guide that would cause the tip of the puncturing needle to move from the defined puncturing entrance point, and
  wherein the retainer has internal threads that mate with corresponding external threads on an upper part of the needle guide such that the needle guide is rotated to tighten and loosen the retainer to secure the needle guide in the fixed position.

8. The puncturing guide according to claim 7, wherein the first section essentially has a shape of a first semi-sphere, having a center in a same level as an underside of the base plate, wherein said center coincides with a point that coincides with the defined puncturing entrance point, and wherein the second section essentially has a shape of a second semi-sphere having a center that coincides with the center of said first semi-sphere.

9. The puncturing guide according to claim 8, wherein the base plate is provided with a central ring-shaped member, in a center of which the first section is provided,
  wherein the second section is provided on a shaft of the needle guide, and
  wherein the first section has a bore extending through the semi-sphere of the first section and the base plate.

10. The puncturing guide according to claim 9, wherein the retainer is adapted to be positioned over the second section and has a through-going opening, said opening has an upper part where the opening is narrowed downwards to a size less than a width of the second section in a plane perpendicular to a main axis of the needle guide, and a lower ring-shaped part, which is provided with an attachment that corresponds to a corresponding attachment on the ring-shaped member on the base plate for securing the needle guide to the base plate.

11. The puncturing guide according to claim 10, wherein an inside of the lower ring-shaped part of the retainer has a shape that corresponds to the shape of the second section.

12. The puncturing guide according to claim 11, wherein the shape of the inside of the lower ring-shaped part of the retainer is chamfered, with the chamfering corresponding to the shape of the second section.

13. The puncturing guide according to claim 11, wherein an outside of the lower ring-shaped part of the retainer is provided with projections that fit into grooves inside the ring-shaped member such that a bayonet coupling between the base plate and the needle guide is provided.

14. A puncturing guide according to claim 11, wherein a part of the needle guide facing the defined puncturing entrance point is reinforced with a reinforcement having an essentially tubular shape.

15. The puncturing guide according to claim 10, wherein an outside of an upper part of the retainer is enlarged to provide a grip for a user.

16. The puncturing guide according to claim 8, wherein the base plate is provided with a number of flat legs for attachment to the patient's skin.

17. The puncturing guide according to claim 16, wherein undersides of said flat legs are provided with a suitable adhesive for attachment to the patient's skin.

18. The puncturing guide according to claim 7, wherein the first section and the second section have shapes of two semi circular equally sized bows pivotally attached to the base plate at positions separated by 90°,
  wherein a slit is provided in each bow, and
  wherein the needle guide is adapted to be arranged in the slits at an intersection point of the bows wherein the needle guide is movable around a point that coincides with the defined puncturing entrance point.

19. The puncturing guide according to claim 7, wherein the internal threads of the retainer fit on the corresponding external threads of the needle guide such that the needle guide can be fixedly secured in a position by tightening the retainer with the needle guide, with the first and second sections being positioned therebetween.

* * * * *